United States Patent
Jones et al.

(10) Patent No.: US 6,420,147 B1
(45) Date of Patent: Jul. 16, 2002

(54) HALOALKALIPHILIC MICROORGANISMS

(75) Inventors: Brian Edward Jones, Va Leidschendam (NL); William Duncan Grant, Leicester (GB)

(73) Assignee: Genencor International, Inc., Rochester, NY (US)

( * ) Notice: Subject to any disclaimer, the term of this patent is extended or adjusted under 35 U.S.C. 154(b) by 0 days.

(21) Appl. No.: 08/186,220

(22) Filed: Jan. 25, 1994

Related U.S. Application Data

(63) Continuation of application No. 08/077,942, filed on Jun. 15, 1993, now abandoned, which is a continuation of application No. 07/789,186, filed on Nov. 7, 1991, now abandoned.

(51) Int. Cl.$^7$ ................................................ C12N 9/14
(52) U.S. Cl. .................... 435/183; 435/252.1; 435/170; 435/195; 435/198; 435/219
(58) Field of Search ............................... 435/252.1, 183, 435/195, 170, 198, 219

(56) References Cited

PUBLICATIONS

Ventura Et Al. *Arch Microb.* 149(4). 1988. pp 273–279 (ABS).*
Imhoff Et Al. *Arch Microb* 114(2). 1977. pp 115–122. (ABS).*
Imhoff Et Al. *Arch Microb* 130(3). 1981. p 238–242. (ABS).*
Imhoff Et Al. *Arch Hyrobiology.* 84(3) 1978. p 381–388 (ABS).*
Danson Et Al. *Biochem Journal.* 218. p 811–818.*
Woese, C.R., et al., "Toward a natural system of organisms: Proposal for the domains Archaea, Bacteria, and Eucarya" (1990) *Proc. Natl. Acad. Sci. U.S.A.*, 87:4576–4579.
Soliman, G.S.H. & Trüper, H.G., "*Halobacterium pharaonis* sp. nov., a New, Extremely Haloalkaliphilic Archaebacterium with Low Magnesium Requirement" (1982) *Zbl. Bakt. Hyg., I. Abt. Orig.* C3:318–329.
Tindall, B.J. & Trüpre, H.G., "Ecophysiology of the Aerobic Halopilic Archaebacteria" (1986) *System. Appl. Microbiol.*, 7:202–212.
Rodriguez–Valera, F. (1988) "Characteristics and Microbhial Ecology of Hypersaline Environments" in Halophilic Bacteria, 1, Rodriguez–Valera, F., ed., CRC Press, Inc., Boca Raton, Florida, pp. 3–30.
Javor, B. (1989) "Solar Salterns" in Hypersaline Environments, Springer–Verlag, Berlin/Heidelberg.
Javor, B. (1989) "Hypersaline, Alkaline Lakes" in Hypersaline Environments, Springer–Verlag, Berlin/Heidelberg.
Wang, D. and Tang, Q., "Natronobacterium from Soda Lakes of China" in Recent Advances in Microbial Ecology (Proceeding of the 5th International Symposium on Microbial Ecology, eds. T. Hattori et al., Japan Scientific Societies Press, Tokyo (1989), pp. 68–72.
Zvyagintseva, I.S. and Tarasor, A.L. (1988) "Extreme Halophilic Bacteria From Saline Solis" *Microbiologiya*, 57:664–669.
Morth, S. and Tindall, B.J. (1985) "Variation of Polar Lipid Composition within Haloalkaliphilic Archaebacteria" *System. Appl. Microbiol.*, 6:247–250.
Upasani, V. and Desai, S. (1990) "Chemical composition of the brines and studies on haloalkaliphilic archaeacteria" *Arch. Microbiol.*, 154:589–593 (Sambhar Salt Lake).
Grant, W.D., Mwatha, W.E. and Jones, B.E. (1990) "Alkaliphiles: ecology, diversity and applications" *FEMS Microbiology Reviews*, 75:255–270.
Grant, W.D. and Tindall, B.J. (1986) "The Alkaline Saline Environment" in Microbes in Extreme Environments (eds. R.A. Herbert and G.A. Codd), Academic Press, London, pp. 22–54.
Tindall, B.J. (1988) "Prokaryotic Life In the Alkaline, Saline, Athalassic Environment" in Halophilic Bacteria, 1:31–70 (ed. F. Rodriguez–Valera), CRC Press Inc., Boca Raton, Florida.
Horikoshi, K. and Akiba, T. (1982) "A New Microbial World" in Alkalophilic Microorganisms (Springer–Verlag, Berlin/Heidelberg/New York).
Shiba, H. (1991) "New Strictly Anaerobic Halophiles and Halopiles and Haloalkaliphiles form Surface Sediments of Hypersaline Enviroments" in Superbugs (eds. K. Horikoshi and W.D. Grant), Japan Scientific Societies Press, Tokyo, and Springer–Verlag, Berlin, Heidelberg, New York, pp. 191–211.
Nakatsugawa, N., (1991) "Novel Methanogenic Archaebacteria Which Grow in Extreme Environments" in Superbugs (eds. K. Horikoshi and W.D. Grant), Japan Scientific Societies Press, Tokyo, and Springer–Verlag, Berlin, Heidelberg, New York, pp. 212–220.
Biosis Previews Database, Philadelphia, Biosis No. 88100773, Ivanova II; et al., & Mikrobiologiya 58 (2), 1989, 251–255, abstract.
Biosis Previews Database, Philadelphia, Biosis No. 89030525, Meyer B; Imhoff J.F. & J Gen Microbiol 135 (11) 1989, 2829–2836, abstract.
Biosis Previews Database, Philadelphia, Biosis No. 78046408, Danson M.j. et al., & Biochem J 218 (3), 1984, 811–818, abstract.
Biosis Previews Database, Philadelphia, Biosis No. 90003116, Davis J.E.; Jones L.P.; Zajic J.E. & ACTA Biotechnol 10 (1) 1990 99–104 abstract.

* cited by examiner

*Primary Examiner*—Leon B. Lankford, Jr.
(74) *Attorney, Agent, or Firm*—Morrison & Foerster LLP

(57) ABSTRACT

Haloalkaliphilic bacteria have been isolated from samples of soil, water, sediment, trona (NaHCO$_3$.Na$_2$CO$_3$.2H$_2$O) and a number of other sources obtained from in and around hypersaline soda lakes. These bacteria have been analyzed according to the principles of numerical taxonomy with respect to each other, as well as to other known haloalkaliphilic bacteria. In addition, these bacteria are further circumscribed by chemotaxonomic analysis. The bacteria produce various alkali- and salt-tolerant enzymes which may be used in various industrial processes requiring such enzymatic activity in a high pH, saline environment.

6 Claims, 2 Drawing Sheets

HALOALKALIPHILIC MICROORGANISMS

This application is a continuation of application Ser. No. 08/077,942, filed 15 June 1993, now abandoned, which is a continuation of Ser. No. 07/789,186 filed 7 November 1991 now abandoned.

The present invention is in the field of microbiology and more particularly in the field of halophilic, alkaliphilic microorganisms.

BACKGROUND OF THE INVENTION

Alkaliphilic microorganisms are defined as organisms which exhibit optimum growth in an alkaline pH environment, particularly in excess of pH 8, and generally in the range between pH 9 and 10. Alkaliphiles may also be found living in environments having a pH as high as 12. Obligate alkaliphiles are incapable of growth at neutral pH.

Alkaliphiles may be found in such everyday environments as garden soil, where transient alkaline conditions may arise due to biological activity such as ammonification, sulphate reduction or photosynthesis. A much richer source of a greater variety of alkaliphilic organisms may be found in naturally occurring, stable alkaline environments such as soda lakes.

Halophilic bacteria are defined as microorganisms that grow optimally in the presence of salt (sodium chloride). Since microorganisms are often capable of growth over a wide range of salt concentrations, the term halophile is usually reserved for microorganisms having a minimum requirement in excess of the concentration found in sea water (ca. 0.5 M or 3%).

Extremely halophilic bacteria are defined as bacteria that grow optimally at above 20% NaCl (3–4 molar). Extreme halophiles inhabit hypersaline environments. The most intensely studied extremely halophilic bacteria belong to the order Halobacteriales. With the exception of the genera Natronobacterium and Natronococcus, all known Halobacteria are obligate halophiles which require at least 12–15% salt for growth and a pH around neutrality. These bacteria belong to the Kingdom Euryarchaeota of the Domain Archaea (the archaeobacteria) (Woese, C. R., et al, Proc. Natl. Acad. Sci. U.S.A., 87, (1990), 4576–4579).

The term "haloalkaliphile" was first used by Soliman and Truper to describe bacteria that are both halophilic and alkaliphilic. (Soliman, G. S. H. & Truper, H. G., (1982), Zbl. Bakt. Hyg., I. Abt. Orig. C3, pp. 318–329). Until now the only known examples of such bacteria belong to the Kingdom Euryarchaeota (Tindall, B. J. & Truper, H. G., (1986), System. Appl. Microbiol., 7, 202–212).

The most extreme hypersaline environments are microbiologically the least diverse but nevertheless contain a distinct, rich and complex flora of extreme halophilic bacteria. It has been suggested that these environments are dominated by the Euryarchaeota with few eubacteria present (Rodriguez-Valera, F., in *Halophilic Bacteria*, vol. 1, (Rodriguez-Valera, F., ed.) CRC Press, Inc., Boca Raton, Fla., (1988), pp. 3–30).

Soda lakes, an example of naturally-occurring alkaline environments which may also be hypersaline, are found in various locations around the world. They are caused by a combination of geological, geographical and climatic conditions. They are characterized by the presence or large amounts of sodium carbonate (or complexes of this salt) formed by evaporation concentration, as well as the corresponding lack of $Ca^{2+}$ and $Mg^{2+}$ which would remove carbonate ions as insoluble salts.

In situations where the concentrations of $Ca^{2+}$ and $Mg^{2+}$ exceed that of carbonate, or where they are equimolar, a salt lake is generated with pH 6–8, and whose ion composition is dependent on the local geology. The Dead Sea in Israel is a typical example of a slightly acidic (pH 6–7) saline lake enriched with divalent cations, particularly $Mg^{2+}$. On the other hand, the Great Salt Lake in Utah, U.S.A. is an example of a $Mg^{2+}$-depleted brine and is slightly alkaline (pH 7–8).

The commercial production of common salt from sea water in solar evaporation ponds (salterns) generates man-made hypersaline environments. Salterns provide excellent model systems over a range of salinities (from sea water to super-saturation), and their chemistry and microbiology have been intensely studied (Javor, B., in *Hypersaline Environments*, Springer-Verlag, Berlin/Heidelberg, 1989).

The African Rift Valley is probably unusual in having lakes with significant, largely permanent bodies of brine. The Kenyan-Tanzanian section of the Rift Valley contains a number of alkaline soda lakes with a range of total salinities from around 5% (w/v) in the more dilute lakes (e.g. Elmenteita, Bogoria, Nakuru, etc.), to saturation (30% or greater) in parts of lakes Magadi, Little Magadi (Nasikie Engida) and Natron. These lakes are devoid of significant amounts of $Ca^{2+}$ and $Mg^{2+}$ (in most cases below the level of detection) and have pH values in the range from 9 to above 11.5 in the most concentrated lakes.

Despite this apparently harsh environment, soda lakes are nevertheless home to a large population of prokaryotes, a few types of which may dominate as permanent or seasonal blooms. The organisms range from alkaliphilic cyanobacteria to haloalkaliphilic archaeobacteria. At the higher salinities (characterized by higher conductivities) haloalkaliphilic archaeobacteria predominate. Moreover, it is not unusual to find common types of alkaliphilic organisms inhabiting soda lakes in various widely dispersed locations throughout the world such as in the East African Rift Valley, in the western U.S., Tibet, China and Hungary. For example, natronobacteria have been isolated and identified from soda lakes and soils located in China (Wang, D. and Tang, Q., "Natronobacterium from Soda Lakes of China" in *Recent Advances in Microbial Ecology* (Proceedings of the 5th International Symposium on Microbial Ecology, eds. T. Hattori et al., Japan Scientific Societies Press, Tokyo, (1989), pp. 68–72), the Soviet Union (Zvyagintseva, I. S. and Tarasor, A. L. (1988) Microbiologiya, 57, 664–669) and in the western U.S. (Morth, S. and Tindall, B. J. (1985) System. Appl. Microbiol., 6, 247–250). Natronobacteria have also been found in soda lakes located in Tibet (W. D. Grant, unpublished observations) and India (Upasani, V. and Desai, S. (1990) Arch. Microbiol., 154, pp. 589–593).

A more detailed study of soda lakes and alkaliphilic organisms in general is provided in Grant, W. D., Mwatha, W. E. and Jones, B. E. (1990) FEMS Microbiology Reviews, 75, 255–270, the text of which is hereby incorporated by reference. Lists of alkaline soda lakes may be found in the publications of Grant, W. D. and Tindall, B. J. in *Microbes in Extreme Environments*, (eds. R. A. Herbert and G. A. Codd); Academic Press, London, (1986), pp. 22–54); and Tindall, B. J. in *Halophilic Bacteria*, Volume 1, (ed. F. Rodriguez-Valera); CRC Press Inc., Boca Raton, Fla., (1988), pp. 31–70, both texts are also hereby incorporated by reference. A detailed study of hypersaline environments is provided in Javor, B., in *Hypersaline Environments*, supra).

Alkaliphiles isolated from non-saline environments are also discussed by Horikoshi, K. and Akiba, T. in *Alkalophilic*

*Microorganisms* (Springer-Verlag, Berlin/Heidelberg/N.Y., 1982). However, alkaliphilic organisms from saline environments such as soda lakes are not discussed therein. Strictly anaerobic bacteria from alkaline, hypersaline environments have been recently described by Shiba, H., in *Superbugs* (eds. K. Horikoshi and W. D. Grant); Japan Scientific Societies Press, Tokyo, and Springer-Verlag, Berlin, Heidelberg, N.Y., (1991), pp. 191–211; and by Nakatsugawa, N., ibid, pp. 212–220.

Alkaliphiles have already made an impact in the application of biotechnology for the manufacture of consumer products. Alkaliphilic enzymes produced by alkaliphilic microorganisms have already found use in industrial processes and have considerable economic potential. For example, these enzymes are currently used in detergent compositions and in leather tanning, and are foreseen to find applications in the food, waste treatment and textile industries. Additionally, alkaliphiles and their enzymes are potentially useful for biotransformations, especially in the synthesis of pure enantiomers. Also, many of the microorganisms described herein are brightly pigmented and are potentially useful for the production of natural colorants.

SUMMARY OF THE INVENTION

The present invention provides pure cultures of novel haloalkaliphilic bacteria. These bacteria have been isolated from samples of soil, water, sediment, trona ($NaHCO_3.Na_2CO_3.2H_2O$) and a number of other sources, all of which were obtained from in and around alkaline, hypersaline lakes. These haloalkaliphiles have been analyzed according to the principles of numerical taxonomy with respect to each other and also to other known haloalkaliphilic bacteria in order to confirm their novelty. In addition, these bacterial taxa are further circumscribed by chemotaxonomic analysis.

The present invention also provides data as to the composition of the environments from which the samples containing the microorganisms were obtained, as well as the media required for their efficient isolation and culturing such that one of ordinary skill may easily locate such an environment and be able to, isolate the organisms of the present invention by following the procedures described herein.

It is also an object of the present invention to provide microorganisms which produce useful alkali- and salt-tolerant enzymes, as well as methods for obtaining substantially pure preparations of these enzymes. These enzymes are capable of performing their functions in high pH, saline environments which makes them uniquely suited for applications requiring such extreme conditions. For example, enzymes having alkali- and salt-tolerance may be employed in detergent compositions, in leather tanning and in the food, waste treatment and textile industries, as well as for biotransformations such as the production of pure enantiomers.

DETAILED DESCRIPTION OF THE INVENTION

Sampling

Several hundreds of strains of bacteria have been isolated from samples of soil, water, sediment, trona ($NaHCO_3.Na_2CO_3.2H_2O$) and a number of other sources in and around alkaline, hypersaline lakes. These samples were obtained as part of an investigation over a period of three years. The isolated bacteria are non-phototrophic eubacteria and archaeobacteria. Up until now, only a few haloalkaliphilic archaeobacteria have been well characterized (see Table 4).

The samples were collected in sterile plastic bags. Sampling was conducted at lakes Magadi, Little Magadi (Nasikie Engida) and Natron, all of which are located in Kenyan-Tanzanian Rift Valley of East Africa. Alkaline soda lakes having similar environments may also be found in Tibet, China, Egypt and the western U.S. At each sampling site, physical parameters such as pH, conductivity and temperature were measured as well as the physical appearance of the site and the sample. Some of the samples were treated locally within 36 hours of collection of the sample but the majority were examined off-site, several weeks after collection.

Table 1 lists various strains which have been isolated. The strains are listed according to the location from which the sample was taken and the physical appearance of the sample itself. Table 2 provides examples of chemical analyses of the lake waters at the sampling locations at the time of extraction of the samples. These data are consistent with earlier analyses (Grant, W. D. and Tindall, B. J., in *Microbes in Extreme Environments*, (eds. R. A. Herbert and G. A. Codd); Academic Press, London, 1986).

Figure 1:
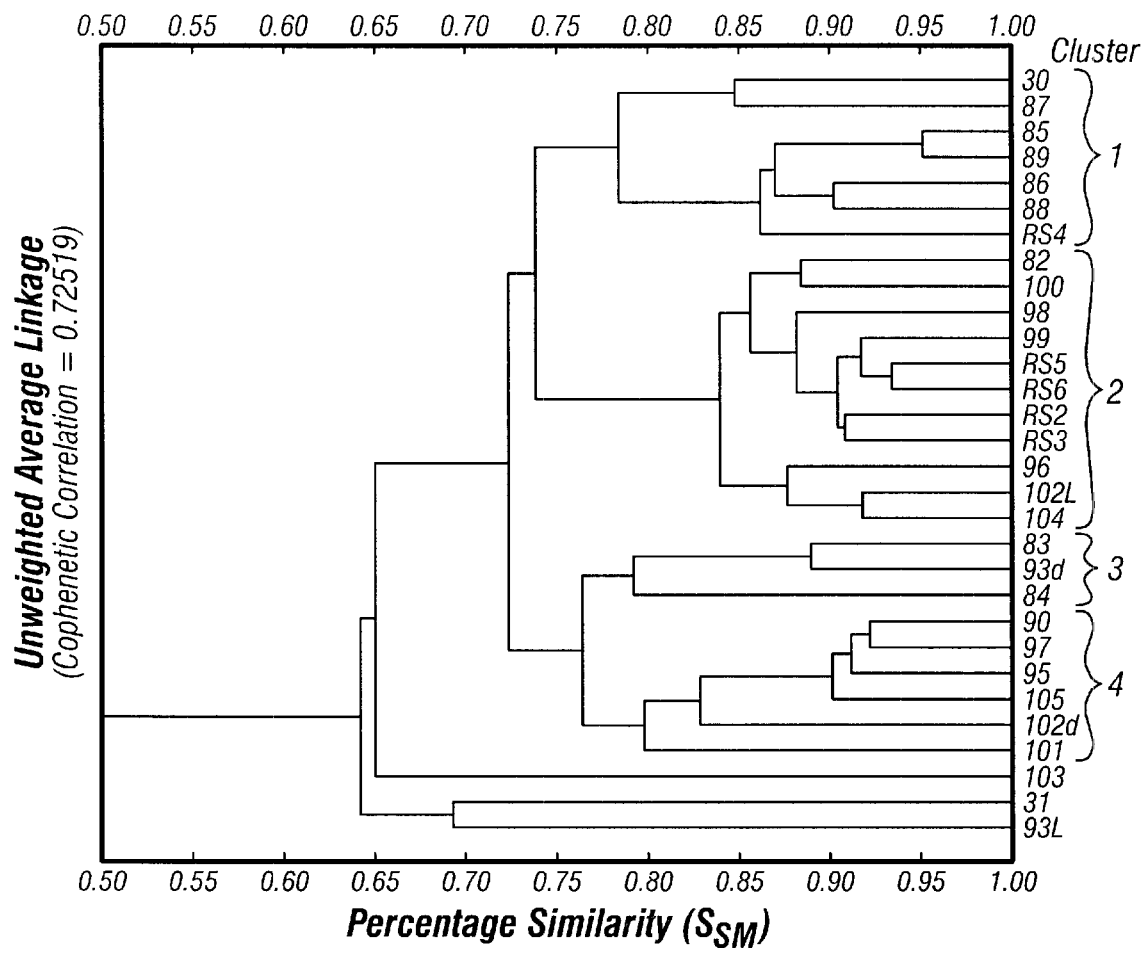
FIG. 1. Dendrogram showing clusters (phenons) obtained with the $S_{SM}$ coefficient and Unweighted Average Linkage procedure.

Table 3 provides a list of the isolated strains arranged according to the results of the numerical taxonomic analysis (FIG. 1). Furthermore Table 3 provides physical properties of the sample, in particular the temperature., conductivity and alkaline pH, as well as the numerous isolation media employed for obtaining pure cultures of the new bacteria. These media are letter coded with reference to Appendix A.

Tables 1, 2 and 3 provide data from which the environment of the sampling locations may be characterized. The chemical and physical analysis of the samples confirm the presence of alkaline pH, as well as the presence of unusually high levels of $Na_2CO_3$, coupled with low levels of $Ca^{2+}$ and $Mg^{2+}$. It is known that the basic environments of soda lakes are stable with respect to their pH and ionic composition. Moreover, the microbial populations found at these sites remain largely stable. Thus, it is to be expected that the environment from which bacteria according to the present invention may be obtained may be determined from the data presented in Tables 1–3.

TABLE 1

Alkaliphilic Strains Arranged According to Their Place of Origin

| STRAINS | SAMPLE LOCATION | SAMPLE APPEARANCE | ANALYSIS |
|---|---|---|---|
| 30M.11, 31M.1 86M.4, 87M.4 | Lake Magadi (final salt making pond) | Liquor and salts | 1 |
| 82M.4 | Lake Magadi (south causeway pumping | Black liquor | 2 |
| 83M.4 | station) | Surface trona crust | |
| 84M.4 | Lake Magadi (pre-concentration salt pan Pl) | Red liquor and salts | 3 |
| 85M.4 | Lake Magadi ("fish water canal") | Water and sediment | 4 |
| 88M.4 | Lake Magadi (salt factory) | "coarse salt" | |

TABLE 1-continued

Alkaliphilic Strains Arranged According to Their Place of Origin

| STRAINS | SAMPLE LOCATION | SAMPLE APPEARANCE | ANALYSIS |
|---|---|---|---|
| 89M.4 | Lake Magadi (upper NW arm) | Water and sediment | 5 |
| 90M.4 | Lake Magadi (upper NW arm) | Soda crust and mud | |
| 93dLM.4, 931LM.4 | Little Lake Magadi (north west springs) | Soda encrusted mud | |
| 95LM.4, 96LM.4 | Little Lake Magadi (south east lagoon) | Water + sediment + trona crust | 6 |
| 97Nt.4, 98Nt.4 | Lake Natron (East shore, lake-basin-margin soda spring | Spring water and surrounding sediment | 7 |
| 99Nt.4 | Lake Natron (dried lake bed, littoral zone) | Black soda mud | |
| 100Nt.4 | | Dried soda crust | |
| 101Nt.4, 102dNt.4, 102lNt.4, 103Nt.4 | Lake Natron (soda seep) | Algal mat + water Soda crusts | |
| 104Nt.4 | Stream flowing to lake | Orange surface scum and water | 8 |
| 105Nt.4 | Pool in stream | Water and sediment | 9 |

TABLE 2

Chemical Analysis of Kenyan-Tanzanian Soda Lake Waters

| ANALYSIS | $Na^+$ | $K^+$ | $Ca^{2+}$ | $Mg^{2+}$ | $SiO_2$ | $PO_4^{3-}$ | $Cl^-$ | $SO_4^{2-}$ | $CO_3^{2-}$ | TON* | TA# |
|---|---|---|---|---|---|---|---|---|---|---|---|
| 1 | 9.22 | 238.9 | <0.01 | 0.008 | 28.30 | 0.13 | 3.49 | 53.62 | 4.92 | 3.86 | 4900 |
| 2 | 7.00 | 57.0 | <0.01 | 0.008 | 14.88 | 1.82 | 3.15 | 17.49 | 3.90 | 1.50 | 4260 |
| 3 | 7.57 | 66.5 | <0.01 | 0.008 | 16.98 | 1.79 | 2.65 | 11.56 | 4.12 | 1.50 | 4490 |
| 4 | 1.34 | 11.89 | 0.015 | 0.008 | 2.78 | 0.46 | 5.41 | 2.60 | 0.65 | 0.69 | 851 |
| 5 | 1.63 | 11.89 | 0.097 | 0.016 | 3.55 | 0.15 | 0.56 | 6.98 | 1.12 | 3.57 | 1110 |
| 6 | 4.63 | 61.13 | 0.017 | 0.029 | 7.54 | 0.31 | 1.86 | 13.12 | 2.43 | 15.07 | 2710 |
| 7 | 0.52 | 4.60 | 0.027 | 0.004 | 0.91 | 0.42 | 0.18 | 5.00 | 0.23 | 0.30 | 365 |
| 8 | 1.22 | 11.51 | 0.142 | 0.025 | 0.77 | 1.18 | 0.39 | 14.78 | 0.63 | 1.43 | 832 |
| 9 | 4.52 | 43.73 | 0.042 | 0.025 | 3.05 | 4.21 | 1.46 | 1.67 | 2.67 | 3.00 | 3040 |

Note: Cations and anions given in millimoles (mM) except for $Na^+$, $Cl^-$ and $CO_3^{2-}$ which are in moles (M)
*TON = Total Organic Nitrogen (mM)
TA = Total Alkalinity in milliequivalents/liter

TABLE 3

ORIGIN OF THE STRAINS ARRANGED BY CLUSTER

| CLUSTER | STRAIN | LOCATION | pH | Temp. °C. | Conductivity mS/cm | ISOLATION MEDIUM |
|---|---|---|---|---|---|---|
| 1 | 30M.4 | Magadi | 12.5 | 55 | 60 | A |
| 1 | 87M.4 | Magadi | 12.3 | 56 | >100 | B |
| 1 | 85M.4 | Magadi | 10.5 | 33 | 80.4 | B |
| 1 | 89M.4 | Magadi | 10.5 | 30 | 60–90 | B |
| 1 | 86M.4$^{CT}$ | Magadi | 12.3 | 56 | >100 | B |
| 1 | 88M.4 | Magadi | NR | NR | NR | B |
| 2 | 82M.4 | Magadi | 12 | 48 | 87 | B |
| 2 | 100Nt.4 | Natron | NR | NR | NR | B |
| 2 | 98Nt.4$^{CT}$ | Natron | 10–10.5 | 35 | 35 | C |
| 2 | 99Nt.4 | Natron | NR | 45 | NR | C |
| 2 | 96LM.4 | Little Magadi | 11 | 37 | >100 | D |
| 2 | 102lNt.4 | Natron | NR | NR | NR | B |
| 2 | 104Nt.4 | Natron | 10–10.5 | NR | 45 | B |
| 3 | 83M.4 | Magadi | NR | NR | NR | C |
| 3 | 93dLM.4$^{CT}$ | Little Magadi | NR | NR | NR | E |
| 3 | 84M.4 | Magadi | 12 | 44 | 87.5 | B |
| 4 | 90M.4 | Magadi | NR | NR | NR | E |
| 4 | 95LM.4$^{CT}$ | Little Magadi | 11 | 37 | >100 | F |
| 4 | 97Nt.4 | Natron | 10–10.5 | 35 | 35 | C |
| 4 | 105Nt.4 | Natron | 11 | 44 | 60–90 | B |
| 4 | 102dNt.4 | Natron | NR | NR | NR | B |
| 4 | 101Nt.4 | Natron | 11 | 40 | 26–36 | C |
| — | 103Nt.4 | Natron | NR | NR | NR | B |
| — | 31M.4 | Magadi | 12.5 | 55 | 60 | A |
| — | 931LM.4 | Little Magadi | NR | NR | NR | E |

*Clusters of microorganisms are obtained by analysis according to the principles of numerical taxonomy using the $S_{SM}$/UPGMA method (see discussion below and FIG. 1).
NR = not tested
The letter codes given for the Isolation Media refer to Appendix A.

Treatment of the Samples: Enrichment and Isolation of Haloalkaliphilic Bacteria A diversity of enrichment and isolation methods were applied. Some of the methods were specifically designed for the enrichment and isolation of haloalkaliphilic bacteria which exhibit specific types of enzyme activity at an alkaline pH. Other techniques of a more general nature were applied for the isolation of diverse sorts of haloalkaliphilic bacteria. In some cases, the specific conditions prevailing in the lakes (Table 2) were taken into account when experiments were performed for the isolation of bacteria.

The different nutrient media employed for the isolation of the new haloalkaliphilic bacteria are designated Medium A–Medium F. The composition of the various media employed is shown in Appendix A.

For the isolation of non-specific haloalkaliphilic organotrophic bacteria, soda lake water samples, or dilutions thereof were streaked out on an alkaline, saline nutrient agar, pH 10–pH 10.5 (Medium A). Samples of a more solid consistency, mud, sediment, etc. were first suspended in an alkaline, saline nutrient broth (Medium A) before spreading on an alkaline, saline nutrient agar (Medium A). The bacteria were cultivated in a heated incubator, preferably at 37° C. In some cases, the samples were suspended in an alkaline, saline nutrient broth (Medium A) and the bacteria cultivated by shaking, preferably at 37° C. for 2–7 days before spreading the broth onto an alkaline, saline nutrient agar (Medium A) for the isolation of bacterial colonies.

For the isolation of haloalkaliphilic bacteria exhibiting specific types of enzyme activity, samples were spread onto alkaline, saline nutrient agar containing specific substrates such as lactalbumin or casein. In some instances, the bacteria in the sample may be enriched for 1 day or several weeks in a non-specific alkaline, saline nutrient broth such as Medium A before spreading the broth onto an alkaline, saline nutrient agar specific for the detection of bacteria exhibiting enzyme activity such as proteolytic activity.

Taxonomic Analysis

Twenty-five strains of bacteria isolated from in an around alkaline, hypersaline lakes were assigned to the category haloalkaliphile on the basis of their ability to grow in a NaCl concentration of 15% or more and at greater than pH 10.

The 25 strains were tested for 107 characters. For practical purposes the characters were divided into 123 character states. The results were analyzed using the principles of numerical taxonomy (Sneath, P. H. A. and Sokal, R. R., in *Numerical Taxonomy*, W. H. Freeman & Co., San Francisco, 1973). The characters tested and manner of testing are compiled in Appendix B. In addition, Appendix C records how each character state was coded for taxonomic analysis.

As controls, 5 known haloalkaliphilic archaeobacteria were subjected to the same analysis using the same conditions. These reference bacteria are the only available known haloalkaliphilic bacteria. These 5 known reference bacteria are recorded in Table 4 from which it will be seen that the "Type Strain" of the known species has been used where available.

TABLE 4

Haloalkaliphilic Reference Strain*

| RS2 | *Natronobacterium gregoryi*[T] | NCIMB 2189 |
| RS3 | *Natronobacterium magadii*[T] | NCIMB 2190 |
| RS4 | *Natronobacterium pharaonis* | NCIMB 2191 |

TABLE 4-continued

Haloalkaliphilic Reference Strain*

| RS5 | *Natronobacterium pharaonis*[T] | DSM 2160 |
| RS6 | *Natronococcus occltus*[T] | NCIMB 2192 |

Figure 2:
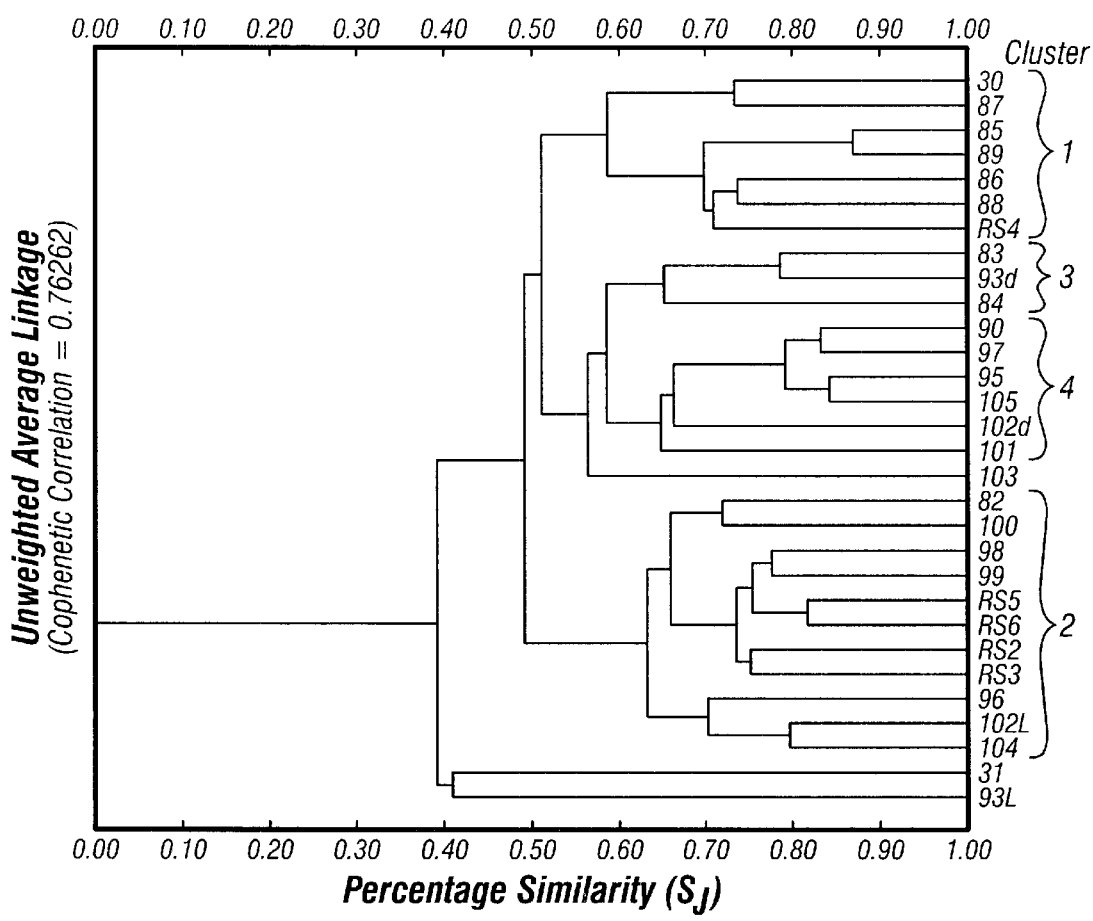
FIG. 2. Dendrogram showing clusters (phenons) obtained with the $S_J$ coefficient and Unweighted Average Linkage procedure.

*abbreviations are as used in FIG. 1 and FIG. 2.
[T]denotes "Type Strain"

Analysis of Test Data

The Estimation of Taxonomic Resemblance

The phenetic data, consisting of 107 characters was scored for 123 two-state characters (presence-absence characters) using binary notation as indicated in Appendix C. Additive scaling was used where appropriate (e.g. growth on NaCl) and where necessary qualitative multistate characters (e.g. colony color) were sub-divided into several mutually exclusive character states. The data was set out in the form of an "n×t" matrix, whose t columns represent the t bacterial strains which are to be grouped on the basis of resemblances, and whose n rows are the unit characters. Taxonomic resemblance of the bacterial strains was estimated by means of a similarity coefficient (Sneath, P. H. A. and Sokal, R. R., *Numerical Taxonomy*, supra, pp. 114–187). Although many different coefficients have been used for biological classification, only a few have found regular use in bacteriology. We have chosen to apply two association coefficients (Sneath, P. H. A. and Sokal, R. R., ibid, p. 129 et seq.), namely, the Simple Matching and Jaccard coefficients. These have been frequently applied to the analysis of bacteriological data and have a wide acceptance by those skilled in the art since they have been shown to result in robust classifications.

The coded data were analyzed using the TAXPAK program package (Sackin, M. J., "Programmes for classification and identification". *In Methods in Microbiology*, Volume 19 (eds. R. R. Colwell and R. Grigorova), pp. 459–494, Academic Press, London, 1987) run on a DEC VAX computer system at the University of Leicester, U.K. In addition, the data were analyzed using the NTSYS-pc (version 1.50) program package run on a IBM PS/2 desk top computer (Rolf, F. J., Numerical taxonomy and multivariate analysis system, Applied Biostatistics Inc. and Exeter Publishing Ltd., Setauket, N.Y., 1988).

A similarity matrix was constructed for all pairs of strains using the Simple Matching Coefficient ($S_{SM}$), (Sneath, P. H. A. and Sokal, R. R., *Numerical Taxonomy*, p. 132; W. H. Freeman & Company, San Francisco, 1973) using the RTBNSIM program in TAXPAK. Cluster analysis of the similarity matrix was accomplished using the Unweighted Pair Group Method with Arithmetic Averages (UPGMA) algorithm, also known as the Unweighted Average Linkage procedure by running the SMATCLST sub-routine in TAXPAK.

The result of the cluster analysis is a dendrogram which is provided in FIG. 1. The dendrogram illustrates the levels of similarity between the bacterial strains. The dendrogram is obtained by using the DENDGR program in TAXPAK.

The phenetic data were re-analyzed using the Jaccard Coefficient ($S_J$) (Sneath, P. H. A. and Sokal, R. R., *Numerical Taxonomy*, p. 131; W. H. Freeman & Company, San Francisco, 1973) by running the RTBNSIM program in TAXPAK. A further dendrogram was obtained by using the SMATCLST with UPGMA option and DENDGR sub-routines in TAXPAK and is illustrated in FIG. 2.

Results of the Cluster Analysis
$S_{SM}$/UPGMA Method

FIG. 1 illustrates the results of the cluster analysis, based on the Simple Matching coefficient and the UPGMA algorithm, of 25 new, haloalkaliphilic bacteria isolated from in and around alkaline lakes, together with 5 known haloalkaliphilic bacteria.

Four natural clusters or phenons of haloalkaliphilic are generated at the 78.5% similarity level. These four clusters include 22 of the 25 new, haloalkaliphilic bacteria isolated from alkaline lakes. Although the choice of 78.5% for the level of delineation may seem arbitrary, it is in keeping with current practices in numerical taxonomy (Austin, B. and Priest, F., in *Modern Bacterial Taxonomy*, p. 37; Van Nostrand Reinhold; Wokingham, U.K., (1986). Placing the delineation at a lower percentage would combine groups of clearly unrelated organisms whose definition is not supported by the data, while a higher percentage would produce a multitude of less well defined clusters. Furthermore, an inspection of the original data, especially the colony characteristics-and the antibiotic sensitivity, indicates that Cluster 1 and Cluster 2 contain exclusively archaeobacteria, and that Cluster 3 and Cluster 4 contain only eubacteria. This conclusion is supported by chemotaxonomic evidence (see discussion below). The group membership of the clusters is further confirmed by the pattern of clusters obtained using the Jaccard coefficient (see below and FIG. 2).

At the 78.5% level, 2 of the clusters (Cluster 3 and Cluster 4) exclusively contain novel haloalkaliphilic eubacteria representing 9 of the newly isolated strains, and these may represent new taxa. Three of the new haloalkaliphilic strains fall outside the major clusters. These non-clustering strains are 103Nt.4, 31M.4 and 931LM.4 and their interrelationships are more difficult to define, but they probably represent new phenons presently not described.

The distribution of positive characters in the clusters is given in Appendix E.

$S_J$/UPGMA Method

The Jaccard coefficient is a useful adjunct to the Simple Matching coefficient as it can be used to detect phenons in the latter due to undue weight being attached to negative matching data. Consequently, the Jaccard coefficient is useful for confirming the validity of clusters defined initially by the use of the Simple Matching coefficient. The Jaccard coefficient is particularly useful in comparing biochemically unreactive or slow growing organisms (Austin, B. and Priest, F., supra, p. 37).

The 4 clusters generated by the $S_{SM}$/UPGMA method are recovered fully in the dendrogram produced by the $S_J$/UPGMA method (FIG. 2). Although there is some rearrangement in the pattern of the clusters, the group memberships remain the same in both dendrograms. However, in this case the clusters are defined at the 59% ($S_J$) level (the minimum required to define Cluster 1 ($S_{SM}$) in which case the (eubacterial) Clusters 3 and 4 are combined. Although this could indicate that these two clusters are differentiated mainly on matching negative characters, an examination of both original dendrograms suggests that a more likely explanation is the heterogeneity of Cluster 1. Strains 30M.4 and 87M.4 appear to form a sub-group within Cluster 1.

When the phenetic data was examined using the NTSYS programmes exactly the same result was achieved for the clustering of the strains.

Determination of Representative Strains

The centroid of each individual cluster generated by the $S_{SM}$/UPGMA method was computed using the RGROUPS program in TAXPAK. The centroid of a cluster of points representing real organisms projected into hyperspace represents a hypothetical average organism. The centroid rarely, if ever, represents a real organism. Therefore, the Euclidean distances of each of the members of the cluster from the centroid of the cluster were calculated in order to establish which organism was closest to the hypothetical average organism. The organism closest to the centroid was designated the "centrotype organism" (indicated with the superscript "CT").

The centrotype organism can be thought of as the "Type Strain" which most closely represents the essential and discriminating features of each particular cluster. The centrotype strains are recorded in Table 5.

TABLE 5

Centrotype Strains

| Cluster Number | Number of Strains in Cluster | Mean Euclidean Distance of Strains from Centroid | Standard Deviation | Strain | Euclidean Distance from Centroid |
|---|---|---|---|---|---|
| 1 | 7 | 3.14 | 0.72 | 86M.4 | 1.79 |
| 2 | 11 | 2.85 | 0.36 | 98Nt.4 | 2.14 |
| 3 | 3 | 3.61 | 1.08 | 93dLM.4 | 1.53 |
| 4 | 6 | 2.55 | 0.41 | 95LM.4 | 1.60 |

Description of Centrotype Strains

Strain 86M.4

An aerobic, coccoid bacterium. No spores observed.

Haloalkaliphile. Grows at pH 10 on a medium containing 20% NaCl. Grows in the presence of 12–30% NaCl.

On alkaline, saline, nutrient-agar (Medium A) forms salmon-pink colored, circular colonies, about 2 mm in diameter, which have a convex elevation and entire margin.

Temperature: grows optimally at 30–40° C. Growth at 20° C. but not at 45° C.

KOH Test: negative

Aminopeptidase Test: negative

Oxidase Reaction: negative

Catalase Reaction: positive

Hydrolysis of Gelatin: negative

Hydrolysis of Starch: negative

Growth is not inhibited by the antibiotics: gentamicin, ampicillin, penicillin G, chloramphenicol, streptomycin, tetracycline, oleandomycin, polymixin, rifampicin, neomycin, vancomycin and kanamycin. Growth is inhibited by the antibiotics: erythromycin, novobiocin and bacitracin.

Chemoorganotroph. Grows on complex substrates such as yeast extracts, peptones and casamino acids.

The membrane lipids contain glycerol diether moieties, indicating the archaeobacteria nature of strain 86M.4.

Strain 98Nt.4

An aerobic, coccoid bacterium. No spores observed.

Haloalkaliphile. Grows at pH 10 on a medium containing 20% NaCl. Grows in the presence of 12–30% NaCl.

On alkaline, saline, nutrient-agar (Medium A) forms opaque, friable, pink colored, circular colonies, 1–2 mm in diameter, which have a convex elevation and entire margin.

Temperature: grows optimally at 30–40° C. Growth at 20° C. but not at 45° C.

KOH Test: positive

Aminopeptidase Test: negative

Oxidase Reaction: positive

Catalase Reaction: positive

Hydrolysis of Gelatin: positive

Hydrolysis of Starch: positive

Growth is not inhibited by the antibiotics: gentamicin, ampicillin, penicillin G, chloramphenicol, streptomycin, tetracycline, oleandomycin, polymixin, neomycin, vancomycin and kanamycin. Growth is inhibited by the antibiotics: erythromycin, novobiocin, rifampicin and bacitracin.

Chemoorganotroph. Grows on complex substrates such as yeast extracts, peptones and casamino acids.

Strain 93dLM.4

An aerobic, Gram-negative, rod-shaped bacterium. No spores observed.

Haloalkaliphile. Grows at pH 10 on a medium containing 20% NaCl. Grows in the presence of 15–30% NaCl.

On alkaline, saline, nutrient-agar (Medium A) forms opaque, mucoid, red colored, circular colonies, about 1 mm in diameter, which have a convex elevation and entire margin.

Temperature: grows optimally at 30–40° C. Growth at 20° C. but not at 45° C.

KOH Test: positive

Aminopeptidase Test: negative

Oxidase Reaction: negative

Catalase Reaction: positive

Hydrolysis of Gelatin: positive

Hydrolysis of Starch: positive

Growth is not inhibited by the antibiotics: streptomycin, tetracycline, polymixin, neomycin and kanamycin. Growth is inhibited by the antibiotics: gentamicin, ampicillin, penicillin G, erythromycin, novobiocin, oleandomycin, rifampicin, vancomycin and bacitracin.

Chemoorganotroph. Grows on complex substrates such as yeast extracts, peptones and casamino acids.

Strain 95LM.4

An aerobic, Gram-negative, rod-shaped bacterium. No spores observed.

Haloalkaliphile. Grows at pH 10 on a medium containing 20% NaCl. Grows in the presence of 8–30% NaCl.

On alkaline, saline, nutrient-agar (Medium A) forms opaque, yellow colored, circular colonies, about 2 mm in diameter, which have a convex elevation and entire margin.

Temperature: grows optimally at 30–40° C. Growth at 20° C. but not at 45° C.

KOH Test: positive

Aminopeptidase Test: negative

Oxidase Reaction: negative

Catalase Reaction: positive

Hydrolysis of Gelatin: positive

Hydrolysis of Starch: negative

Growth is not inhibited by the antibiotics: gentamicin, streptomycin, tetracycline, polymixin, neomycin and kanamycin. Growth is inhibited by the antibiotics: ampicillin, penicillin G, chloramphenicol, erythromycin, novobiocin, oleandomycin, rifampicin, vancomycin and bacitracin.

Chemoorganotroph. Grows on complex substrates such as yeast extracts, peptones and casamino acids.

Non-clustering Strains

The strains which do not fall into the four clusters defined here are also novel bacteria not previously known or described. These strains, coded 103Nt.4, 31M.4 and 931LM.4 may represent rarer varieties of haloalkaliphilic bacteria. A description of these "non-clustering" strains has been made so as to be able to distinguish these organisms from all other bacteria previously known and described.

Strain 103Nt.4

An aerobic, Gram-negative, rod-shaped bacterium. No spores observed.

Haloalkaliphile, grows at pH 10 on a medium containing 20% NaCl. Grows in presence of 0–30% NaCl.

On alkaline, saline, nutrient-agar (Medium A) forms opaque orange colored, circular colonies, 2–3 mm in diameter, which have a convex elevation and entire margin.

Temperature: grows optimally at 30–40° C. Growth at 20° C. but not at 45° C.

KOH test: positive

Aminopeptidase test: negative

Oxidase reaction: negative

Catalase reaction: positive

Hydrolysis of Gelatin: positive

Hydrolysis of Starch: positive

Growth is not inhibited by the antibiotics: gentamicin, chloramphenicol, fusidic acid, erythromycin, methicillin, oleandomycin, rifampicin, vancomycin, and bacitracin. Growth is inhibited by the antibiotics: nitrofurantoin, amipicillin, nalidixic acid, sulphamethoxazole, trimethoprim, penicillin G, novobiocin, streptomycin, tetracycline, polymixin, neomycin, and kanamycin.

Chemoorganotroph. Grows on complex substrates such as yeast extract, peptones and casamino acids. Growth is stimulated by a variety of simple sugars, amino acids and organic acids.

The membrane lipids are based on fatty acid esters indicating the eubacterial nature of Strain 103Nt.4.

Strain 31M.4

An aerobic, Gram-positive, rod-shaped bacterium. No spores observed.

Obligate haloalkaliphile, grows at pH 10 on a medium containing 20% NaCl. Grows in the presence of 15–30% NaCl. No growth in 12% NaCl.

On alkaline, saline, nutrient-agar (Medium A) forms cream colored, circular colonies, about 1 mm in diameter, which have a convex elevation and entire margin.

Temperature: grows optimally at 30–40° C. Grows at 20° C. and 45° C., but not at 50° C.

KOH test: negative

Aminopeptidase test: negative

Oxidase reaction: negative

Catalase reaction: negative

Hydrolysis of Starch: positive

Grows is not inhibited by the antibiotics: sulphamethoxazole, trimethoprim, polymixin, rifampicin, and bacitracin. Growth is inhibited by the antibiotics: gentamicin, nitrofurantoin, ampicillin, nalidixic acid, penicillin G, chloramphenicol, erythromycin, fusidic acid, methicillin, novobiocin, streptomycin, tetracycline, and oleandomycin.

Chemoorganotroph. Grows on complex substrates such as yeast extract, peptones and casamino acids.

The membrane lipids contain glycerol diether moieties indicating the archaeobacterial nature of Strain 31M.4.

Strain 931LM.4

An aerobic, Gram-variable, coccoid bacterium. No spores observed.

Haloalkaliphile, grows at pH 10 on a medium containing 20% NaCl. Grows in presence of 0–30% NaCl.

On alkaline, saline, nutrient-agar (Medium A) forms pink colored, irregular colonies, 1–2 mm in diameter, which have a raised elevation and entire margin.

KOH test: positive

Oxidase reaction: negative

Hydrolysis of Starch: positive

Growth is not inhibited by the antibiotics: nitrofurantoin and trimethoprim.

Growth is inhibited by the antibiotics: gentamicin, ampicillin, nalidixic acid, penicillin G. chloramphenicol, erythromycin, fusidic acid, methicillin, novobiocin, streptomycin, tetracycline.

Chemoorganotroph. Grows on complex substrates such as yeast extract, peptones and casamino acids.

The membrane lipids contain glycerol diether moieties indicating the archaeobacterial nature of Strain 931LM.4.

Chemotaxonomic Definition of the Clusters

Chemotaxonomy is the study of the chemical variations of cells in relation to systematics. The analysis of chromosomal DNA, ribosomal RNA, proteins, cell walls and membranes, for example, can give valuable insights into taxonomic relationships and may be used as a further tool to classify or to verify the taxonomy of microorganisms (Goodfellow, M. and Minnikin, D. E. in *Chemical Methods in Bacterial Systematics,* (eds. Goodfellow, M. and Minnikin, D. E.), Academic Press, London and Orlando, Fla., (1985), pp. 1–15).

Analysis of Core Lipids

All membrane lipids of the archaeobacteria identified to date are characterized by unusual structural features, which can be considered to be specific taxonomic markers for this group of microorganisms. While all living organisms so far known have membrane lipids based on ester linkages, the archaeobacteria have lipids based on ether linkages. (De Rosa, M. et al, (1986), Microbiological Reviews, 50, 70–80).

The membrane lipids were extracted from bacteria and analyzed by this layer chromatography according to the methods described by Ross, H. N. M. et al, ((1981), Journal of General Microbiology, 123, 75–80).

The results of this analysis for representative strains of the haloalkaliphilic bacteria of the present invention are set out in Table 6. These show clearly that the strains of Cluster 1 and Cluster 2 lack fatty acid methyl esters, but contain glycerol diethyl moieties characteristic of the archaeobacteria. The strains of Cluster 3 and Cluster 4 contain fatty acid methyl esters but no glycerol diethyl moieties, thus confirming their identity as eubacteria. These results further underline a fundamental difference between the bacteria of Clusters 1 and 2 and Clusters 3 and 4.

TABLE 6

Core Lipids of Haloalkaliphilic Bacteria

| CLUSTER | STRAIN | CORE LIPID |
|---|---|---|
| 1 | 30M.4 | GDEM |
|  | 87M.4 | GDEM |
|  | 89M.4 | GDEM |
|  | 86M.4$^{CT}$ | GDEM |
|  | 88M.4 | GDEM |
| 2 | 82M.4 | GDEM |
|  | 100Nt.4 | GDEM |
|  | 99Nt.4 | GDEM |
|  | 96LM.4 | GDEM |
|  | 102lNt.4 | GDEM |
|  | 104Nt.4 | GDEM |
| 3 | 84M.4 | FAME |
| 4 | 90M.4 | FAME |

TABLE 6-continued

Core Lipids of Haloalkaliphilic Bacteria

| CLUSTER | STRAIN | CORE LIPID |
|---|---|---|
|  | 105Nt.4 | FAME |
|  | 101Nt.4 | FAME |
| — | 103Nt.4 | FAME |
| — | 31M.4 | GDEM |
| — | 931LM.4 | GDEM |

GDEM = glycerol diether moieties
FAME = fatty acid methyl esters

Production and Application of Alkali- and Salt-tolerant Enzymes

The haloalkaliphilic microorganisms of the present invention produce a variety of enzymes (c.f. Appendices D and E). These enzymes are capable of performing their functions at an extremely high pH and high salt concentrations, making them uniquely suited for their application in a variety of processes requiring such enzymatic activity in such environments or reaction conditions.

Examples of the various applications for enzymes having alkali- and salt-tolerance are in detergent compositions, leather tanning, food treatment, waste treatment and in the textile industry. These enzymes may also be used for biotransformations, especially in the preparation of pure enantiomers.

The haloalkaliphiles may easily be screened for the production of alkali- and salt-tolerant enzymes having, for example, lipolytic, proteolytic, starch-degrading or other activities using the methods described in Appendix B.

The broth in which haloalkaliphilic bacteria are cultured typically contains one or more types of enzymatic activity. The broth containing the enzyme or enzymes may be used directly in the desired process after the removal of the bacteria therefrom by means of centrifugation or filtration, for example.

If desired, the culture filtrate may be concentrated by freeze drying, before or after dialysis, or by ultrafiltration. The enzymes may also be recovered by precipitation and filtration. Alternatively, the enzyme or enzymes contained in the broth may be isolated and purified by chromatographic means or by gel electrophoresis, for example, before being applied to the desired process.

The genes encoding these alkali- and salt-tolerant enzymes may be isolated, cloned and brought to expression in compatible expression hosts to provide a source of larger volumes of enzyme products which may be, if desired, more easily purified and used in a desired industrial application, should the wild-type strain fail to produce sufficient amounts of the desired enzyme, or does not ferment well.

In one embodiment, the enzymatic preparation may be used in wash tests to determine the efficacy of the enzymatic activity.

Enzyme preparations from the haloalkaliphilic bacteria may be tested in a specially developed mini-wash test using cotton swatches soiled, for example, with protein-, lipid- and/or starch-containing components. Prior to the wash test, the swatches can be pre-treated with a solution containing an anionic surfactant, sodium perborate and a bleach activator (TAED). After this treatment, the test swatches are rinsed in running demineralized water and air-dried. This treatment results in the fixation of the soil, making its removal more difficult.

The washing tests may be performed using a defined detergent composition plus a specific amount of enzymatic activity in the presence of the test swatches. After washing, the swatches are rinsed in running demineralized water and air-dried. The reflectance of the test swatches is measured with a photometer.

APPENDIX A

Media Used in the Present Invention

MEDIUM A

| | | |
|---|---|---|
| Yeast Extract (Difco: Detroit, MI, USA) | 10.0 | $gl^{-1}$ |
| Casamino Acids (Difco) | 7.5 | $gl^{-1}$ |
| Trisodium citrate | 3.0 | $gl^{-1}$ |
| KCl | 2.0 | $gl^{-1}$ |
| $MgSO_4.7H_2O$ | 1.0 | $gl^{-1}$ |
| $MnCl_2.4H_2O$ | 0.00036 | $gl^{-1}$ |
| $FeSO_4.7H_2O$ | 0.05 | $gl^{-1}$ |
| NaCl | 200.0 | $gl^{-1}$ |
| $Na_2CO_3$ | 18.5 | $gl^{-1}$ |
| Agar* | 20.0 | $gl^{-1}$ |

MEDIUM B

| | | |
|---|---|---|
| Yeast Extract | 10.0 | $gl^{-1}$ |
| Casamino Acids | 7.5 | $gl^{-1}$ |
| Trisodium citrate | 3.0 | $gl^{-1}$ |
| KCl | 2.0 | $gl^{-1}$ |
| $MgSO_4.7H_2O$ | 1.0 | $gl^{-1}$ |
| $MnCl_2.4H_2O$ | 0.00036 | $gl^{-1}$ |
| $FeSO_4.7H_2O$ | 0.05 | $gl^{-1}$ |
| NaCl | 200.0 | $gl^{-1}$ |
| $Na_2CO_3$ | 18.5 | $gl^{-1}$ |
| Casein | 20.0 | $gl^{-1}$ |
| Agar | 20.0 | $gl^{-1}$ |

MEDIUM C

| | | |
|---|---|---|
| Yeast Extract | 10.0 | $gl^{-1}$ |
| Casamino Acids | 7.5 | $gl^{-1}$ |
| Trisodium citrate | 3.0 | $gl^{-1}$ |
| KCl | 2.0 | $gl^{-1}$ |
| $MgSO_4.7H_2O$ | 1.0 | $gl^{-1}$ |
| $MnCl_2.4H_2O$ | 0.00036 | $gl^{-1}$ |
| $FeSO_4.7H_2O$ | 0.05 | $gl^{-1}$ |
| NaCl | 200.0 | $gl^{-1}$ |
| $Na_2CO_3$ | 18.5 | $gl^{-1}$ |
| Lactalbumin | 10.0 | $gl^{-1}$ |
| Agar | 20.0 | $gl^{-1}$ |

MEDIUM D

| | | |
|---|---|---|
| Yeast Extract | 0.2 | $gl^{-1}$ |
| Casamino Acids | 0.15 | $gl^{-1}$ |
| Trisodium citrate | 1.5 | $gl^{-1}$ |
| KCl | 2.0 | $gl^{-1}$ |
| $MgSO_4.7H_2O$ | 1.0 | $gl^{-1}$ |
| $MnCl_2.4H_2O$ | 0.00036 | $gl^{-1}$ |
| $FeSO_4.7H_2O$ | 0.05 | $gl^{-1}$ |
| NaCl | 150.0 | $gl^{-1}$ |
| $Na_2CO_3$ | 150.0 | $gl^{-1}$ |
| Casein | 20.0 | $gl^{-1}$ |
| Agar | 20.0 | $gl^{-1}$ |

MEDIUM E

| | | |
|---|---|---|
| Yeast Extract | 0.2 | $gl^{-1}$ |
| Casamino Acids | 0.15 | $gl^{-1}$ |
| Trisodium citrate | 1.5 | $gl^{-1}$ |
| KCl | 2.0 | $gl^{-1}$ |
| $MgSO_4.7H_2O$ | 1.0 | $gl^{-1}$ |
| $MnCl_2.4H_2O$ | 0.00036 | $gl^{-1}$ |
| $FeSO_4.7H_2O$ | 0.05 | $gl^{-1}$ |
| NaCl | 150.0 | $gl^{-1}$ |
| $Na_2CO_3$ | 150.0 | $gl^{-1}$ |
| Lactalbumin | 10.0 | $gl^{-1}$ |
| Agar | 20.0 | $gl^{-1}$ |

MEDIUM F

| | | |
|---|---|---|
| Glucose | 0.2 | $gl^{-1}$ |
| Peptone (Difco) | 0.1 | $gl^{-1}$ |
| Yeast Extract | 0.1 | $gl^{-1}$ |

APPENDIX A-continued

Media Used in the Present Invention

| | | |
|---|---|---|
| $K_2HPO_4$ | 1.0 | $gl^{-1}$ |
| $MgSO_4.7H_2O$ | 0.2 | $gl^{-1}$ |
| NaCl | 40.0 | $gl^{-1}$ |
| $Na_2CO_3$ | 10.0 | $gl^{-1}$ |
| Casein | 20.0 | $gl^{-1}$ |
| Agar | 20.0 | $gl^{-1}$ |

*(when required for a solid medium)

Appendix B

Methods for Unit Tests

1. Character Numbers 1 to 12

Colony color. size, form, elevation. margin

A suspension of bacteria was spread over an alkaline, saline, nutrient agar (Medium A) and cultivated at 37° C. Colonies were examined after 7 to 14 days.

2. Character Numbers 13 to 15

Cell morphology. Gram's stain reaction

Bacterial cells were cultivated in alkaline, saline, nutrient broth (Medium A without agar) until adequate growth was obtained. The cells were spun down in a centrifuge and resuspended in a small amount of fresh medium. A drop of the bacterial suspension was allowed to air-dry on a microscope slide. The Gram's staining test was performed using the Dussault modification (Journal of Bacteriology, 70, 484–485, 1955) with safranin as counterstain.

3. Character Number 16

KOH test

The test was performed using 3% KOH in 20% NaCl+1% $Na_2CO_3$ on 7 to 14 days old bacterial cultures grown on alkaline, saline, nutrient agar (Medium A) as described by Halebian et al., in Journal of Clinical Micro-biology, 13, 444–448, 1981 and compared with the reaction in solution containing only 20% NaCl+1% $Na_2CO_3$.

4. Character Number 17

Aminoreptidase reaction

The test was performed using the diagnostic test strips Bactident® Aminopeptidase (E. Merck, Darmstadt, Germany). A yellow color within 30 minutes was recorded as a positive reaction.

5. Character Number 18

Oxidase reaction

Filter paper moistened with a 1% aqueous solution of N,N,N¹,N¹-tetramethyl-p-phenylenediamine or, oxidase identification discs (bioMérieux: Charbonieres-les-Bains, France) were smeared with a young bacterial culture from alkaline, saline, nutrient agar. A purple color within 1 minute was recorded as a positive reaction. *E. coli* was used as a negative control.

6. Character Number 19

Catalase reaction

A bacterial colony from alkaline, saline, nutrient agar was suspended in a drop of 3% hydrogen peroxide solution, or "1D color catalase" reagent (bioMérieux). Bubbles of oxygen released was recorded as a positive reaction.

7. Character Number 20

Gelatin hydrolysis

Charcoal-gelatin discs (bioMérieux) or "chargels" (Oxoid) were incubated at 37° C. in an alkaline, saline, nutrient broth (Medium A) together with bacteria. A black sediment indicated a positive reaction.

8. Character Number 21 and 39
Skim milk and starch hydrolysis test

Bacteria were inoculated on to alkaline, saline, nutrient agar (Medium A) supplemented with 5.0 g/l skim powder or 2.0 g/l starch, and incubated at 37° C. Areas of clearing around bacterial colonies in an otherwise opaque agar were recorded as a positive reaction. Zones of starch hydrolysis were confirmed by staining with iodine solution (lugol).

9. Character Numbers 22–29
NaCl tolerance

Two methods were applied.
(a) Bacterial strains were cultivated at 37° C. on an alkaline, nutrient agar (Medium A) containing 0%, 4%, 8%, 12%, 15%, 20%, 25% or 30% (w/v) NaCl. The agar plates were examined for bacterial growth after 7–14 days.
(b) Bacterial strains were cultivated at 37° C. in an alkaline nutrient broth (Medium A) containing 0%, 4%, 8%, 12%, 15%, 20%, 25% or 30% (w/v) NaCl.

Bacterial growth was monitored regularly up to 14 days by optical density measurements using a Klett meter (green filter).

10. Bacterial Numbers 30 and 31
Growth temperature

Bacterial strains were inoculate in alkaline, saline, nutrient broth (Medium A) and incubated at 10° C., 15° C., 20° C., 45° C. or 50° C. Bacterial growth was monitored regularly up to 14 days by optical density measurements using a Klett meter (green filter).

11. Character Numbers 32–38
Carbohydrate utilisation

A minimal medium composed (g/l distilled water) of yeast extract, 1.0; $KNO_3$, 1.0; KCl, 2.0; $MgSO_4.7H_2O$, 1.0; $MnCl_2.4H_2O$, 0.00036; $FeSO_4.7H_2O$, 0.05; NaCl, 200.0; $Na_2CO_3$, 18.5; agar, 20.0 was supplemented with 2.0 g/l of the carbohydrate under test and poured into square Petri dishes.

Bacteria were inoculated, using a 25 point multi-point inoculator, from 1.0 ml of a bacterial suspension in an alkaline, saline, nutrient broth (Medium A). The agar-plates were incubated at 37° C. for up to 14 days. The results were recorded by comparing bacterial growth on minimal nutrient medium containing a carbohydrate supplement with growth on a minimal medium without the carbohydrate under test.

12. Character Numbers 40–51
Amino acids as carbon and nitrogen source

The same technique was employed as for tests 32–38.

13. Character Numbers 52–70
Enzymatic activities

Use was made of the commercially available test strip APIZYM (API-bioMérieux) which was used according to the manufacturer's instructions, except that the haloalkaliphilic bacterial cells were suspended in alkaline, saline, nutrient broth (Medium A). The strips were incubated at 37° C. for 4 hours.

14. Character Numbers 71–91
Antibiotic sensitivity

A light suspension of bacteria in alkaline, saline, nutrient broth was spread on the surface of alkaline nutrient, saline agar (Medium A) and allowed to dry. Commercially available antibiotic susceptibility test disks (Oxoid or Mast Laboratories: Merseyside, U.K.) were applied to the agar surface. The bacteria were cultivated at 37° C. for up to 14 days. Clear zones around the antibiotic disks indicated sensitivity and were recorded as positive.

15. Character Numbers 92–123
Growth on carbon substrates

Use was made of the commercially available test strip ATB 32 GN (API-bioMérieux: La Balme les Grottes, France). The strips were used according to the manufacturer's instructions but with the addition of 1.0 ml of a solution containing 20% NaCl and 1% $Na_2CO_3$ to the vials of basal medium provided. The strips were incubated at 37° C. for 48 hours.

APPENDIX C

Unit Tests for Analysis by Numerical Taxonomy

| TEST | CHARACTER NUMBER | CHARACTER STATE | POSITIVE (present) | NEGATIVE (absent) |
|---|---|---|---|---|
| Colony color | 1 | yellow | 1 | 0 |
|  | 2 | cream/beige | 1 | 0 |
|  | 3 | orange | 1 | 0 |
|  | 4 | pink/red | 1 | 0 |
| Colony size in (diameter mm) | 5 | ≦1 mm | 1 | 0 |
|  | 6 | >1 mm | 1 | 0 |
| Colony form | 7 | circular | 1 | 0 |
|  | 8 | punctiform | 1 | 0 |
|  | 9 | irregular | 1 | 0 |
| Colony elevation | 10 | convex | 1 | 0 |
|  | 11 | raised | 1 | 0 |
| Colony margin | 12 | entire | 1 | 0 |
| Cell morphology | 3 |  | rod = 1 | coccus = 0 |
| Gram's stain | 14 | Gram positive | 1 | 0 |
|  | 15 | Gram negative | 1 | 0 |
| KOH test | 16 |  | 1 | 0 |
| Aminopeptidase reaction | 17 |  | 1 | 0 |
| Oxidase reaction | 18 |  | 1 | 0 |
| Catalase reaction | 19 |  | 1 | 0 |
| Gelatin hydrolysis | 20 |  | 1 | 0 |
| Skim milk test | 21 |  | 1 | 0 |
| NaCl tolerance | 22 | growth at 0% | 1 | 0 |
|  | 23 | growth at 4% | 1 | 0 |
|  | 24 | growth at 8% | 1 | 0 |
|  | 25 | growth at 12% | 1 | 0 |
|  | 26 | growth at 15% | 1 | 0 |
|  | 27 | growth at 20% | 1 | 0 |
|  | 28 | growth at 25% | 1 | 0 |
|  | 29 | growth at 30% | 1 | 0 |
| Growth temperature | 30 | growth at ≦20° C. | 1 | 0 |
|  | 31 | growth at ≧45° C. | 1 | 0 |
| Carbohydrate utilization | 32 | Fumerate | 1 | 0 |
|  | 33 | Fructose | 1 | 0 |
|  | 34 | Succinate | 1 | 0 |
|  | 35 | Formate | 1 | 0 |
|  | 36 | Lactose | 1 | 0 |
|  | 37 | Galactose | 1 | 0 |
|  | 38 | Xylose | 1 | 0 |
|  | 39 | Starch | 1 | 0 |
| Amino acids as carbon and nitrogen sources | 40 | Serine | 1 | 0 |
|  | 41 | Proline | 1 | 0 |
|  | 42 | Asparagine | 1 | 0 |
|  | 43 | Arginine | 1 | 0 |
|  | 44 | Alanine | 1 | 0 |
|  | 45 | Lysine | 1 | 0 |
|  | 46 | Methionine | 1 | 0 |
|  | 47 | Phenylalanine | 1 | 0 |

APPENDIX C-continued

Unit Tests for Analysis by Numerical Taxonomy

| TEST | CHARACTER NUMBER | CHARACTER STATE | | POSITIVE (present) | NEGATIVE (absent) |
|---|---|---|---|---|---|
| | 48 | Glycine | | 1 | 0 |
| | 49 | Valine | | 1 | 0 |
| | 50 | Glutamate | | 1 | 0 |
| | 51 | Leucine | | 1 | 0 |
| Enzymatic activity | 52 | Alkaline phosphatase | | 1 | 0 |
| | 53 | Esterase (C4) | | 1 | 0 |
| | 54 | Esterase lipase (C8) | | 1 | 0 |
| | 55 | Lipase (C14) | | 1 | 0 |
| | 56 | Leucine arylamidase | | 1 | 0 |
| | 57 | Valine arylamidase | | 1 | 0 |
| | 58 | Cystine arylamidase | | 1 | 0 |
| | 59 | Trypsin | | 1 | 0 |
| | 60 | Chymotrypsin | | 1 | 0 |
| | 61 | Acid phosphatase | | 1 | 0 |
| | 62 | Naphthol-AS-BI-phosphohydrolase | | 1 | 0 |
| | 63 | α-galactosidase | | 1 | 0 |
| | 64 | β-galactosidase | | 1 | 0 |
| | 65 | β-glucuronidase | | 1 | 0 |
| | 66 | α-glucosidase | | 1 | 0 |
| | 67 | β-glucosidase | | 1 | 0 |
| | 68 | N-acetyl-β-glucosaminidase | | 1 | 0 |
| | 69 | α-mannosidase | | 1 | 0 |
| | 70 | α-fucosidase | | 1 | 0 |
| Antibiotic sensitivity (inhibition of growth = positive) | 71 | Gentamicin | 10 μg | 1 | 0 |
| | 72 | Nitrofurantoin | 50 μg | 1 | 0 |
| | 73 | Ampicillin | 25 μg | 1 | 0 |
| | 74 | Nalidixic Acid | 30 μg | 1 | 0 |
| | 75 | Sulphmethoxazole | 50 μg | 1 | 0 |
| | 76 | Trimethoprim | 25 μg | 1 | 0 |
| | 77 | Penicillin G | 10 IU | 1 | 0 |
| | 78 | Chloramphenicol | 25 μg | 1 | 0 |
| | 79 | Erythromycin | 5 μg | 1 | 0 |
| | 80 | Fusidic Acid | 10 μg | 1 | 0 |
| | 81 | Methicillin | 10 μg | 1 | 0 |
| | 82 | Novobiocin | 5 μg | 1 | 0 |
| | 83 | Streptomycin | 10 μg | 1 | 0 |
| | 84 | Tetracycline | 25 μg | 1 | 0 |
| | 85 | Oleandomycin | 5 μg | 1 | 0 |
| | 86 | Polymixin | 300 IU | 1 | 0 |
| | 87 | Rifampicin | 2 μg | 1 | 0 |
| | 88 | Neomycin | 30 μg | 1 | 0 |
| | 89 | Vancomycin | 30 μg | 1 | 0 |
| | 90 | Kanamycin | 30 μg | 1 | 0 |
| | 91 | Bacitracin | 10 IU | 1 | 0 |
| Growth on Carbon Substrates (ATB) | 92 | Rhamnose | | 1 | 0 |
| | 93 | N-acetylglucosamine | | 1 | 0 |
| | 94 | Ribose | | 1 | 0 |
| | 95 | Inositol | | 1 | 0 |
| | 96 | Saccharose | | 1 | 0 |
| | 97 | Maltose | | 1 | 0 |
| | 98 | Itaconate | | 1 | 0 |
| | 99 | Suberate | | 1 | 0 |
| | 100 | Malonate | | 1 | 0 |
| | 101 | Acetate | | 1 | 0 |
| | 102 | Lactate | | 1 | 0 |
| | 103 | Alanine | | 1 | 0 |
| | 104 | Mannitol | | 1 | 0 |
| | 105 | Glucose | | 1 | 0 |
| | 106 | Salicin | | 1 | 0 |
| | 107 | Melibiose | | 1 | 0 |
| | 108 | Fucose | | 1 | 0 |
| | 109 | Sorbitol | | 1 | 0 |
| | 110 | Arabinose | | 1 | 0 |
| | 111 | Propionate | | 1 | 0 |
| | 112 | Caprate | | 1 | 0 |
| | 113 | Valerate | | 1 | 0 |
| | 114 | Citrate | | 1 | 0 |
| | 115 | Histidine | | 1 | 0 |
| | 116 | 5-ketogluconate | | 1 | 0 |
| | 117 | Glycogen | | 1 | 0 |
| | 118 | 3-hydroxybenzoate | | 1 | 0 |
| | 119 | Serine | | 1 | 0 |
| | 120 | 2-ketogluconate | | 1 | 0 |
| | 121 | 3-hydroxybenzoate | | 1 | 0 |
| | 122 | 4-hydroxybutyrate | | 1 | 0 |
| | 123 | Proline | | 1 | 0 |

APPENDIX D

Screening for proteolytic, Amylolytic and Lipolytic Activity

Proteolytic Activity

| STRAIN | LACTALBUMIN | CASEIN | GELATIN |
|---|---|---|---|
| Cluster 1 | | | |
| 30M.4 | n.t. | n.t. | n.t. |
| 87M.4 | n.t. | + | + |
| 85M.4 | n.t. | + | + |
| 89M.4 | n.t. | + | + |
| 86M.4[CT] | n.t. | + | − |
| 88M.4 | n.t. | + | + |
| RS4 | n.t. | n.t. | + |
| Cluster 2 | | | |
| 82M.4 | n.t. | + | + |
| 100Nt.4 | n.t. | + | + |
| 98Nt.4[CT] | + | n.t. | + |
| 99Nt.4 | + | n.t. | − |
| RS5 | n.t. | n.t. | + |
| RS6 | n.t. | n.t. | + |
| RS2 | n.t. | n.t. | + |
| RS3 | n.t. | n.t. | + |
| 96LM.4 | n.t. | + | + |
| 102lNt.4 | n.t. | + | n.t. |
| 104Nt.4 | n.t. | + | + |
| Cluster 3 | | | |
| 83M.4 | + | n.t. | + |
| 93dLM.4[CT] | + | n.t. | + |
| 84M.4 | n.t. | + | − |
| Cluster 4 | | | |
| 90M.4 | + | n.t. | + |
| 95LM.4[CT] | n.t. | + | + |
| 97Nt.4 | + | n.t. | + |
| 105Nt.4 | n.t. | + | + |
| 102dNt.4 | n.t. | + | + |
| 101Nt.4 | + | n.t. | + |
| Non-Clustering Strains | | | |
| 103Nt.4 | n.t. | + | + |
| 31M.4 | n.t. | n.t. | n.t. |
| 93lLM.4 | + | n.t. | n.t. |

Amylolytic and Lipolytic Activity

| STRAIN | STARCH HYDROLYSIS | ESTERASE LIPASE | LIPASE |
|---|---|---|---|
| Cluster 1 | | | |
| 30M.4 | − | + | − |
| 87M.4 | + | + | − |
| 85M.4 | − | + | − |
| 89M.4 | + | + | − |
| 86M.4[CT] | − | + | − |
| 88M.4 | − | + | − |

APPENDIX D-continued

Screening for proteolytic, Amylolytic and Lipolytic Activity

| | | | |
|---|---|---|---|
| RS4 | − | + | − |

Cluster 2

| | | | |
|---|---|---|---|
| 82M.4 | − | + | − |
| 100Nt.4 | − | + | − |
| 98Nt.4[CT] | + | + | − |
| 99Nt.4 | + | + | − |
| R55 | − | + | − |
| RS6 | + | + | − |
| RS2 | − | + | − |
| RS3 | − | + | − |
| 96LM.4 | − | + | + |
| 102lNt.4 | − | + | + |
| 104Nt.4 | − | + | − |

Cluster 3

| | | | |
|---|---|---|---|
| 83M.4 | + | + | − |
| 93dIM.4[CT] | + | + | − |
| 84M.4 | + | + | − |

Cluster 4

| | | | |
|---|---|---|---|
| 90M.4 | − | + | − |
| 95LM.4[CT] | − | + | − |
| 97Nt.4 | − | + | − |
| 105Nt.4 | − | + | − |
| 102dNt.4 | − | + | − |
| 101Nt.4 | − | + | − |

Non-clustering Strains

| | | | |
|---|---|---|---|
| 103Nt.4 | + | + | − |
| 31M.4 | + | + | − |
| 93lLM.4 | + | + | + | n.t. - not tested
Proteolytic Activity determined on media B–F (Appendix A) and according to character 20 (Appendix B).
Starch Hydrolysis determined according to character 39 (Appendix B)
Esterase Lipase Activity determined according to character 54 (Appendix B)
Lipase Activity determined according to character 55 (Appendix B).

APPENDIX E

Distribution of Positive Characters to Clusters of Haloalkaliphilic Bacteria Defined at the 78.5% Similarity Level ($S_{SM}$)

| CHARACTER | 1 | 2 | 3 | 4 |
|---|---|---|---|---|
| Colony color yellow | 0 | 0 | 0 | 67 |
| Colony color cream/beige | 14 | 9 | 33 | 17 |
| Colony color orange | 0 | 0 | 0 | 17 |
| Colony color pink/red | 86 | 91 | 67 | 0 |
| Colony size ≦1 mm | 57 | 91 | 100 | 0 |
| Colony size ≧1 mm | 43 | 9 | 0 | 100 |
| Colony circular | 71 | 82 | 100 | 100 |
| Colony punctiform | 29 | 18 | 0 | 0 |
| Colony irregular | 0 | 0 | 0 | 0 |
| Colony elevation convex | 100 | 100 | 100 | 100 |
| Colony elevation raised | 0 | 0 | 0 | 0 |
| Colony margin entire | 100 | 100 | 100 | 100 |
| Cells rod-shaped | 29 | 36 | 67 | 83 |
| Gram positive | 29 | 27 | 33 | 17 |
| Gram negative | 43 | 82 | 67 | 67 |
| KOH test | 43 | 100 | 100 | 33 |
| Aminopeptidase reaction | 0 | 0 | 0 | 0 |
| Oxidase reaction | 0 | 9 | 0 | 17 |
| Catalase reaction | 100 | 91 | 100 | 100 |
| Gelatin hydrolysis | 71 | 82 | 67 | 100 |
| Skim milk test | 0 | 0 | 0 | 17 |
| Growth at 0% NaCl | 0 | 0 | 0 | 17 |
| Growth at 4% NaCl | 0 | 9 | 33 | 33 |
| Growth at 8% NaCl | 29 | 18 | 33 | 83 |
| Growth at 12% NaCl | 86 | 100 | 67 | 100 |
| Growth at 15% NaCl | 100 | 100 | 100 | 100 |
| Growth at 20% NaCl | 100 | 100 | 100 | 100 |
| Growth at 25% NaCl | 100 | 100 | 100 | 100 |
| Growth at 30% NaCl | 71 | 100 | 100 | 100 |
| Growth at ≦20° C. | 57 | 64 | 100 | 33 |
| Growth at ≧45° C. | 14 | 27 | 33 | 33 |
| Fumarate | 57 | 82 | 67 | 33 |
| Fructose | 43 | 91 | 33 | 33 |
| Succinate | 57 | 82 | 33 | 33 |
| Formate | 0 | 55 | 0 | 0 |
| Lactose | 0 | 0 | 0 | 0 |
| Galactose | 57 | 91 | 67 | 33 |
| Xylose | 29 | 0 | 0 | 17 |
| Starch | 29 | 27 | 100 | 0 |
| Serine | 14 | 9 | 33 | 0 |
| Proline | 57 | 91 | 67 | 33 |
| Asparagine | 0 | 9 | 0 | 0 |
| Arginine | 57 | 91 | 67 | 33 |
| Alanine | 57 | 91 | 67 | 33 |
| Lysine | 43 | 82 | 67 | 0 |
| Methionine | 29 | 18 | 33 | 0 |
| Phenylalanine | 0 | 0 | 0 | 17 |
| Glycine | 0 | 0 | 0 | 0 |
| Valine | 43 | 91 | 33 | 0 |
| Glutamate | 14 | 0 | 33 | 0 |
| Leucine | 0 | 9 | 0 | 0 |
| Alkaline phosphatase | 0 | 27 | 0 | 0 |
| Esterase (C4) | 100 | 100 | 100 | 100 |
| Esterase Lipase (C8) | 100 | 100 | 100 | 100 |
| Lipase (C14) | 0 | 18 | 0 | 0 |
| Leucine arylamidase | 100 | 100 | 100 | 83 |
| Valine arylamidase | 14 | 73 | 0 | 0 |
| Cystine arylamidase | 14 | 18 | 0 | 0 |
| Trypsin | 14 | 9 | 0 | 0 |
| Chymotrypsin | 29 | 36 | 0 | 33 |
| Acid phosphatase | 0 | 18 | 0 | 17 |
| Naphthol-AS-BI-phosphohydrolase | 0 | 27 | 0 | 0 |
| α-galactosidase | 0 | 0 | 0 | 0 |
| β-galactosidase | 0 | 0 | 0 | 0 |
| β-glucuronidase | 0 | 0 | 0 | 0 |
| α-glucosidase | 57 | 55 | 33 | 33 |
| β-glucosidase | 29 | 0 | 0 | 0 |
| N-acetyl-β-glucosaminidase | 0 | 9 | 0 | 0 |
| α-mannosidase | 0 | 0 | 0 | 0 |
| α-fucosidase | 0 | 0 | 0 | 0 |
| Gentamycin | 0 | 0 | 67 | 50 |
| Nitrofurantoin | 43 | 82 | 0 | 0 |
| Ampicillin | 0 | 0 | 100 | 67 |
| Nalidixic Acid | 0 | 18 | 0 | 0 |
| Sulphmethoxazole | 43 | 82 | 0 | 17 |
| Trimethoprim | 57 | 91 | 0 | 17 |
| Penicillin B | 0 | 0 | 100 | 100 |
| Chloramphenicol | 0 | 0 | 100 | 100 |
| Erythromycin | 86 | 73 | 100 | 100 |
| Fusidic Acid | 14 | 9 | 0 | 17 |
| Methicillin | 0 | 0 | 0 | 0 |
| Novobiocin | 100 | 82 | 33 | 100 |
| Streptomycin | 0 | 18 | 67 | 0 |
| Tetracycline | 14 | 9 | 33 | 17 |
| Oleandomycin | 0 | 0 | 100 | 100 |
| Polymixin | 0 | 0 | 0 | 0 |
| Rifampicin | 14 | 64 | 67 | 83 |
| Neomycin | 0 | 0 | 0 | 0 |
| Vancomycin | 0 | 0 | 100 | 83 |
| Kanamycin | 0 | 0 | 0 | 17 |
| Bacitracin | 100 | 82 | 100 | 100 |
| Rhamnose | 57 | 0 | 33 | 0 |
| N-acetylglucosamine | 71 | 0 | 33 | 0 |
| Ribose | 0 | 0 | 33 | 0 |
| Inositol | 71 | 9 | 67 | 0 |
| Saccharose | 71 | 9 | 33 | 33 |
| Maltose | 71 | 9 | 67 | 17 |
| Itaconate | 0 | 0 | 0 | 0 |
| Suberate | 14 | 0 | 33 | 0 |
| Malonate | 71 | 0 | 67 | 0 |
| Acetate | 71 | 0 | 67 | 0 |

APPENDIX E-continued

Distribution of Positive Characters to Clusters of Haloalkaliphilic Bacteria Defined at the 78.5% Similarity Level ($S_{SM}$)

| CHARACTER | 1 | 2 | 3 | 4 |
|---|---|---|---|---|
| Lactate | 71 | 0 | 67 | 0 |
| Alanine | 71 | 9 | 33 | 0 |
| Mannitol | 57 | 0 | 33 | 0 |
| Glucose | 71 | 0 | 33 | 17 |
| Salicin | 29 | 0 | 0 | 0 |
| Melibiose | 57 | 0 | 67 | 0 |
| Fucose | 43 | 0 | 0 | 0 |
| Sorbitol | 43 | 0 | 33 | 0 |
| Arabitol | 43 | 0 | 33 | 0 |
| Propionate | 57 | 0 | 67 | 0 |
| Caprate | 14 | 27 | 0 | 17 |
| Valerate | 57 | 0 | 67 | 0 |
| Citrate | 71 | 0 | 67 | 17 |
| Histidine | 57 | 0 | 67 | 17 |
| 5-ketogluconate | 14 | 0 | 33 | 0 |
| Glycogen | 71 | 9 | 67 | 0 |
| 3-hydroxybenzoate | 0 | 0 | 0 | 0 |
| Serine | 57 | 73 | 67 | 0 |
| 2-ketogluconate | 43 | 73 | 67 | 33 |
| 3-hydroxybutyrate | 71 | 0 | 67 | 17 |
| 4-hydroxybenzoate | 71 | 18 | 67 | 0 |
| Proline | 71 | 55 | 67 | 0 |

What is claimed is:

1. A pure bacterial culture useful for the production of enzymes, wherein the bacteria consist of aerobic, non-phototrophic, haloalkaliphilic bacteria which grow as colonies which are circular, convex, and entire, which bacteria give:
    a) a positive response in the following tests:
        1) KOH test
        2) catalase
        3) growth in 15% to 30% NaCl
        4) growth at 20° C. or less
        5) starch hydrolysis
        6) esterase
        7) esterase lipase
        8) leucine arylamidase;
    b) a negative response to the following tests:
        1) oxidase
        2) growth in 0% NaCl
        3) alkaline phosphatase
        4) acid phosphatase;
    c) growth is inhibited by the antibiotics ampicillin, penicillin G, chloramphenicol, oleandomycin, vancomycin, and bacitracin.

2. A pure bacterial culture useful for the production of enzymes, wherein the bacteria consist of aerobic, non-phototrophic, haloalkaliphilic bacteria which grow as colonies which are circular, convex, and entire, which bacteria give:
    a) a positive response in the following tests:
        1) catalase
        2) gelatin hydrolysis
        3) grows in 12% to 30% NaCl
        4) esterase
        5) esterase lipase;
    b) a negative response to the following tests:
        1) colonies colored red or pink
        2) starch hydrolysis
        3) alkaline phosphatase;
    c) growth is inhibited by the antibiotics penicillin G, chloramphenicol, novobiocin, oleandomycin, and bacitracin.

3. A pure bacterial culture useful for the production of enzymes, wherein the bacteria consist of aerobic, non-phototrophic, Gram-negative, rod shaped, haloalkaliphilic bacteria having the following characteristics:
    a) on akaline, saline, nutrient agar, forms opaque, orange colored circular colonies, 2 to 3 millimeters in diameter, which have a convex elevation and entire margin;
    b) grows at 20° C.;
    c) no growth at 45° C.;
    d) KOH test is positive;
    e) aminopeptidase test is negative;
    f) oxidase test is negative;
    g) catalase test is positive;
    h) grows in presence of 0% to 30% NaCl;
    i) hydrolysis of gelatin is positive;
    j) hydrolysis of starch is positive;
    k) growth is not inhibited by the antibiotics gentamicin, chloramphenicol, fusidic acid, erythromycin, methicillin, oleandomycin, rifampicin, vancomycin, or bacitracin;
    l) growth is inhibited by the antibiotics nitrofurantoin, ampicillin, nalidixic acid, sulfamethizole, trimethoprim, penicillin G, novobiocin, streptomycin, tetracycline, polymyxin, neomycin, or kanamycin;
    m) grows on simple sugars;
    n) grows on amino acids;
    o) grows on organic acids;
    p) grows on yeast extract and peptones; and
    q) contains membrane lipids based on fatty acid esters.

4. A method for the preparation of enzymes comprising:
    a) culturing the bacteria of claim 3 in a culture medium:
    b) separating the bacteria from the culture medium; and
    c) recovering enzyme activity from the culture medium.

5. A method for the preparation of enzymes comprising:
    a) culturing the bacteria of claim 4 in a culture medium:
    b) separating the bacteria from the culture medium; and
    c) recovering enzyme activity from the culture medium.

6. A method for the preparation of enzymes comprising:
    a) culturing the bacteria of claim 5 in a culture medium:
    b) separating the bacteria from the culture medium; and
    c) recovering enzyme activity from the culture medium.

* * * * *